United States Patent
Junger et al.

(10) Patent No.: US 11,076,992 B2
(45) Date of Patent: Aug. 3, 2021

(54) METHODS OF TRANSVERSE PLACEMENT IN ELT

(71) Applicant: ELT SIGHT, INC., Los Angeles, CA (US)

(72) Inventors: Johannes Junger, Gilching (DE); Markus Enders, Munich (DE)

(73) Assignee: ELT Sight, Inc., Los Angeles, CA (US)

( * ) Notice: Subject to any disclaimer, the term of this patent is extended or adjusted under 35 U.S.C. 154(b) by 118 days.

(21) Appl. No.: 16/389,460

(22) Filed: Apr. 19, 2019

(65) Prior Publication Data
US 2020/0330274 A1   Oct. 22, 2020

(51) Int. Cl.
*A61F 9/008* (2006.01)

(52) U.S. Cl.
CPC ............ *A61F 9/00802* (2013.01); *A61F 2009/00868* (2013.01); *A61F 2009/00891* (2013.01)

(58) Field of Classification Search
None
See application file for complete search history.

(56) References Cited

U.S. PATENT DOCUMENTS

| | | | |
|---|---|---|---|
| 4,607,622 A | 8/1986 | Fritch et al. | |
| 5,323,766 A | 6/1994 | Uram | |
| 5,738,677 A | 4/1998 | Colvard et al. | |
| 6,283,974 B1 | 9/2001 | Alexander | |
| 6,743,221 B1 | 6/2004 | Hobart et al. | |
| 2004/0082939 A1 | 4/2004 | Berlin | |
| 2005/0192480 A1 | 9/2005 | Toriya et al. | |
| 2006/0244652 A1 | 11/2006 | Tethrake et al. | |

(Continued)

FOREIGN PATENT DOCUMENTS

| | | |
|---|---|---|
| DE | 19920615 A1 | 12/2000 |
| DE | 10023176 A1 | 11/2001 |

(Continued)

OTHER PUBLICATIONS

Taliaferro, Kevin et al. "Excimer Laser Trabeculostomy Normalizing IOP and Restoring Physiologic Outflow in Glaucoma." Glaucoma Today, 2009, pp. 45-47 (Year: 2009).*

(Continued)

*Primary Examiner* — Paula J Stice
(74) *Attorney, Agent, or Firm* — Greenberg Traurig, LLP; Roman Fayerberg; David J. Dykeman

(57) ABSTRACT

Glaucoma patients suffer from increased intraocular pressure due to blocked fluid flow from the anterior chamber of the eye. Methods of the invention include inserting a probe into an eye of a subject having glaucoma, adjusting placement of the probe to a position transverse to Schlemm's canal in the eye, and applying a plurality of shots from an excimer laser source while the probe is in the transverse position, thereby treating glaucoma by creating a plurality of perforations in Schlemm's canal and/or the trabecular meshwork. By providing a laser probe at a position transverse to Schlemm's canal, energy from the laser is delivered to a greater amount of surface area than if the laser was arranged in a parallel or perpendicular position to Schlemm's canal, resulting in optimal formation of perforations. The perforations allow for drainage of fluid and increased outflow of aqueous humor in the eye.

19 Claims, 7 Drawing Sheets

(56) References Cited

U.S. PATENT DOCUMENTS

| | | |
|---|---|---|
| 2007/0122096 A1 | 5/2007 | Temelkuran et al. |
| 2007/0147752 A1 | 6/2007 | Weisberg et al. |
| 2007/0219601 A1 | 9/2007 | Neuberger |
| 2007/0265602 A1 | 11/2007 | Mordaunt et al. |
| 2008/0054073 A1 | 3/2008 | Charles |
| 2008/0082078 A1* | 4/2008 | Berlin ............... A61F 9/00802 604/521 |
| 2008/0097415 A1 | 4/2008 | Zimare et al. |
| 2008/0108981 A1 | 5/2008 | Telfair et al. |
| 2008/0108983 A1 | 5/2008 | Nadolski |
| 2009/0118715 A1 | 5/2009 | Mansour |
| 2009/0157064 A1 | 6/2009 | Hodel |
| 2010/0019125 A1 | 1/2010 | Stefani et al. |
| 2010/0324543 A1 | 12/2010 | Kurtz et al. |
| 2013/0041357 A1 | 2/2013 | Neuberger |
| 2013/0085484 A1* | 4/2013 | Van Valen ............. A61B 90/30 606/6 |
| 2014/0058367 A1 | 2/2014 | Dantus |
| 2014/0188096 A1 | 7/2014 | Chia et al. |
| 2014/0316388 A1 | 10/2014 | Hipsley |
| 2015/0148615 A1 | 5/2015 | Brennan et al. |
| 2015/0297408 A1 | 10/2015 | Dolzan et al. |
| 2015/0374549 A1 | 12/2015 | Scott |
| 2017/0100041 A1 | 4/2017 | Kasamatsu et al. |
| 2017/0202708 A1 | 7/2017 | Berlin |
| 2017/0304001 A1 | 10/2017 | Searle et al. |
| 2018/0000337 A1 | 1/2018 | Chen et al. |
| 2018/0042772 A1 | 2/2018 | Mansour |
| 2018/0263647 A1 | 9/2018 | Aljuri et al. |
| 2018/0353328 A1 | 12/2018 | Bacher et al. |
| 2018/0360310 A1 | 12/2018 | Berlin |
| 2019/0105200 A1 | 4/2019 | Hipsley |
| 2020/0330157 A1 | 10/2020 | Junger et al. |
| 2020/0330181 A1 | 10/2020 | Junger et al. |
| 2020/0330266 A1 | 10/2020 | Junger et al. |
| 2020/0330275 A1 | 10/2020 | Junger et al. |
| 2020/0330279 A1 | 10/2020 | Junger et al. |
| 2020/0330280 A1 | 10/2020 | Junger et al. |
| 2020/0330281 A1 | 10/2020 | Junger et al. |

FOREIGN PATENT DOCUMENTS

| | | |
|---|---|---|
| EP | 1835862 B1 | 6/2011 |
| WO | 2020215062 A1 | 10/2020 |
| WO | 2020215064 A1 | 10/2020 |
| WO | 2020215066 A1 | 10/2020 |
| WO | 2020215067 A1 | 10/2020 |
| WO | 2020215068 A1 | 10/2020 |
| WO | 2020215071 A1 | 10/2020 |
| WO | 20200215073 A1 | 10/2020 |

OTHER PUBLICATIONS

Crandall, Alan, "Combining Cataract and Glaucoma Surgery", Review of Ophthalmology, 1-4, Jun. 13, 2008.

Grover, Davinder S. "When You Have Cataracts and Glaucoma", Glaucoma Research Foundation, Oct. 29, 2017.

Toteberg-Harms, et al., "Cataract surgery combined with excimer laser trabeculotomy to lower intraocular pressure: effectiveness dependent on preoperative IOP." BMC ophthalmology, vol. 13, No. 1, p. 24 (2013).

Tsai, James C. "High Eye Pressure and Glaucoma", Glaucoma Research Foundation, Oct. 29, 2017.

International Search Report in International Application No. PCT/US2020/028971 dated Aug. 2, 2020.

U.S. Appl. No. 16/389,404 US20200330281A1, filed Apr. 19, 2019 Oct. 22, 2020, Combination Treatment Using Phaco and ELT.

U.S. Appl. No. 16/389,437 US2020030281A1, filed Apr. 19, 2019 Oct. 22, 2020, Excimer Laser Fiber Illumination.

U.S. Appl. No. 16/389,346 US20200330181A1, filed Apr. 19, 2019 Oct. 22, 2020, Authentication Systems and Methods for an Excimer Laser System.

U.S. Appl. No. 16/389,359 US20200330279A1, filed Apr. 19, 2019 Oct. 22, 2020, Calibration System for Improving Manufacture Tolerance in Excimer Laser.

U.S. Appl. No. 16/389,446 US20200330266A1, filed Apr. 19, 2019 Oct. 22, 2020, Combination Treatment Using ELT.

U.S. Appl. No. 16/389,425 US20200330280A1, filed Apr. 19, 2019 Oct. 22, 2020, Personalization of Excimer Laser Fibers.

U.S. Appl. No. 16/389,386 US20200330157A1, filed Apr. 19, 2019 Oct. 22, 2020, Enhances Fiber Probes for ELT.

* cited by examiner

METHODS OF TRANSVERSE PLACEMENT IN ELT

TECHNICAL FIELD

The invention relates generally to excimer laser trabeculostomy (ELT) procedures and fiber probe placement during the procedure.

BACKGROUND

A leading cause of irreversible blindness is glaucoma. Typically, fluid flows freely through the anterior chamber of the eye and exits through a drainage system that includes the trabecular meshwork and Schlemm's canal. When an individual suffers from glaucoma, a blockage in the trabecular meshwork or Schlemm's canal prevents the fluid from draining and results in increased pressure in the eye. If left untreated, the increased pressure in the eye damages the optic nerve, leading to gradual vision loss and eventual blindness.

Traditional methods of treating glaucoma include pharmaceutical treatments, laser treatments, surgical treatments, or combinations thereof to lower pressure in the eye. Pharmaceutical treatments, such as medicated drops, and laser treatments, such as selective laser trabeculoplasty (SLT), often are not effective in treating advanced stages of glaucoma. Invasive surgical treatments, such as placement of implants or drainage stents, are used to treat advanced stages of glaucoma. However, the invasive surgical treatments have drawbacks and require great precision to avoid dislodgement of the implant. For example, if a stent is not placed properly on the first attempt, the stent may be difficult to place at all.

SUMMARY

The invention provides treatment of glaucoma using excimer laser trabeculostomy (ELT). During the ELT procedure, a laser probe is positioned transverse to the Schlemm's canal to create perforations the trabecular meshwork and/or Schlemm's canal. By permanently perforating Schlemm's canal and/or the trabecular meshwork, built-up fluid in the anterior chamber of the eye is immediately allowed to drain. Arrangement of the laser probe at a position transverse to Schlemm's canal provides optimum results by providing a greater amount of surface area for photoablation by the laser. By applying the laser at a position transverse to Schlemm's canal, each laser shot provides photoablation of a greater amount of surface area, resulting in a greater perforation from fewer laser shots.

In open-angle glaucoma (OAG), the obstruction of fluid outflow at the trabecular meshwork and inner wall of Schlemm's canal is the primary cause of elevated intraocular pressure (TOP). The invention uses an excimer laser to perforate the trabecular meshwork and/or Schlemm's canal to create an internal outflow channel, increasing drainage of the fluid known as aqueous humor from the anterior chamber of the eye. The perforations also increase flow of aqueous humor and reduce pressure in the eye.

Methods of the invention use ELT to reestablish outflow of fluid from the anterior chamber of the eye without inciting a healing response at the target tissue. ELT converts trabecular meshwork tissue into gas by photoablation. Ablation with excimer lasers causes almost no thermal damage, thereby minimizing inflammation and formation of scar tissue. Unlike argon and selective laser trabeculoplasty procedures, ELT precisely excises tissue without causing thermal injury or scarring the surrounding tissue. Moreover, other lasers, such as ruby and argon lasers, cannot achieve a permanent perforation of the trabecular meshwork because of inflammatory and healing responses. Due to the lack of inflammation and scar tissue formation, methods of the invention require less recovery time than traditional laser treatments or surgical treatments, such as placement of implants.

During the ELT procedure, a physician guides a delivery tip of a fiber probe through a corneal incision in the eye and towards the trabecular meshwork. In some embodiments, methods of the invention comprise administering anesthesia to the subject before making the incision and inserting the probe. Typically, the incision has a length of about ⅛ inch or smaller. The delivery tip is guided by the physician to a position transverse to the Schlemm's canal. In some embodiments of the invention, the physician uses a light source such as a Gonio lens, endoscope, or other illumination source to aid in positioning the delivery tip. Furthermore, the light source aids the physician in verifying the effectiveness of the laser treatment by visualizing drainage of the aqueous humor and bloody reflux emitted during the treatment.

Once the delivery tip is at a position transverse to the Schlemm's canal, the physician delivers a series of shots of laser energy to the trabecular meshwork. By providing a laser probe at a position transverse to the Schlemm's canal, or crosswise to the Schlemm's canal, energy from the laser is delivered to a greater amount of surface area than if the fiber probe was placed in a parallel or perpendicular position to the Schlemm's canal. Thus, arrangement of the delivery tip at a position transverse to the Schlemm's canal achieves optimal photoablation and perforation formation in the meshwork and/or Schlemm's canal. The creation of a plurality of perforations in leads to immediate drainage of aqueous humor from the anterior chamber of the eye.

ELT treatment creates long-term openings that connect the anterior chamber of the eye directly to Schlemm's canal using an excimer laser. Some embodiments of the invention use a 308-nm xenon-chloride ultraviolet excimer laser, which causes minimal thermal damage compared with visible or infrared lasers. In some embodiments of the invention, the excimer laser is an encapsulated xenon chloride (XeCl) excimer laser such as the EX TRA LASER manufactured by MLase AG. Moreover, to avoid the corneal absorption of laser radiation, an optical fiber is used to deliver the energy from the excimer laser. The delivery tip of the fiber probe comprises the optical fiber jacketed in metal, such as stainless steel. In some examples of the invention, the delivery tip is beveled (e.g., at 0°, 15°, 30°, and 45° with respect to the tip). The fiber probe comprises an optical fiber suitable for UV light that is embedded into a handheld laser applicator. For example, a FIDO LASER APPLICATOR manufactured by MLase AG may be used as the fiber probe.

To achieve easier drainage of the aqueous humor in order to reduce IOP, a total of about 10 ELT perforations, each having a diameter of about 200 μm, are lasered into the trabecular meshwork and/or Schlemm's canal. In comparison, stents and implants have smaller individual diameters that are between about 80 μm to about 120 μm. In some embodiments, about 10 shots from an excimer laser source are applied to each eye. In some embodiments, greater than about 10 shots are applied to each eye. Because ELT is a non-thermal procedure, tissue reactions in the trabecular meshwork are not shown or activated post-operatively. The lack of heat generation in ELT allows for a nearly absent activation of postoperative tissue reactions and provides long-term stability of the pressure-reducing effects. Moreover, unlike the traditional glaucoma treatment method of shunt or stent placement, the stability of Schlemm's canal using ELT treatment remains unchanged.

DETAILED DESCRIPTION

Glaucoma patients suffer from increased intraocular pressure due to a blockage of fluid outflow from the eye. The invention uses an excimer laser to shoot perforations in the Schlemm's canal and/or trabecular meshwork of the eye. ELT treats open-angle glaucoma at the site of occurrence by increasing the permeability of the trabecular meshwork. During ELT, the laser creates a direct connection between the front chamber of the eye and the Schlemm's canal by using a fiber probe in physical contact with the trabecular meshwork.

Methods of the invention include inserting a probe into an eye of a subject having glaucoma, adjusting placement of the probe to a position transverse to Schlemm's canal in the eye, and applying a plurality of shots from an excimer laser source while the probe is in the transverse position, thereby treating glaucoma by creating a plurality of perforations in Schlemm's canal and/or the trabecular meshwork. By providing a laser probe at a position transverse to Schlemm's canal, energy from the laser is delivered to a greater amount of surface area than if the laser was arranged in a parallel or perpendicular position to Schlemm's canal, resulting in optimal formation or perforations. The perforations allow immediate drainage of fluid from the anterior chamber of the eye. The perforations also allow for increased flow of aqueous humor in the eye and reduced intraocular pressure.

Figure 1:
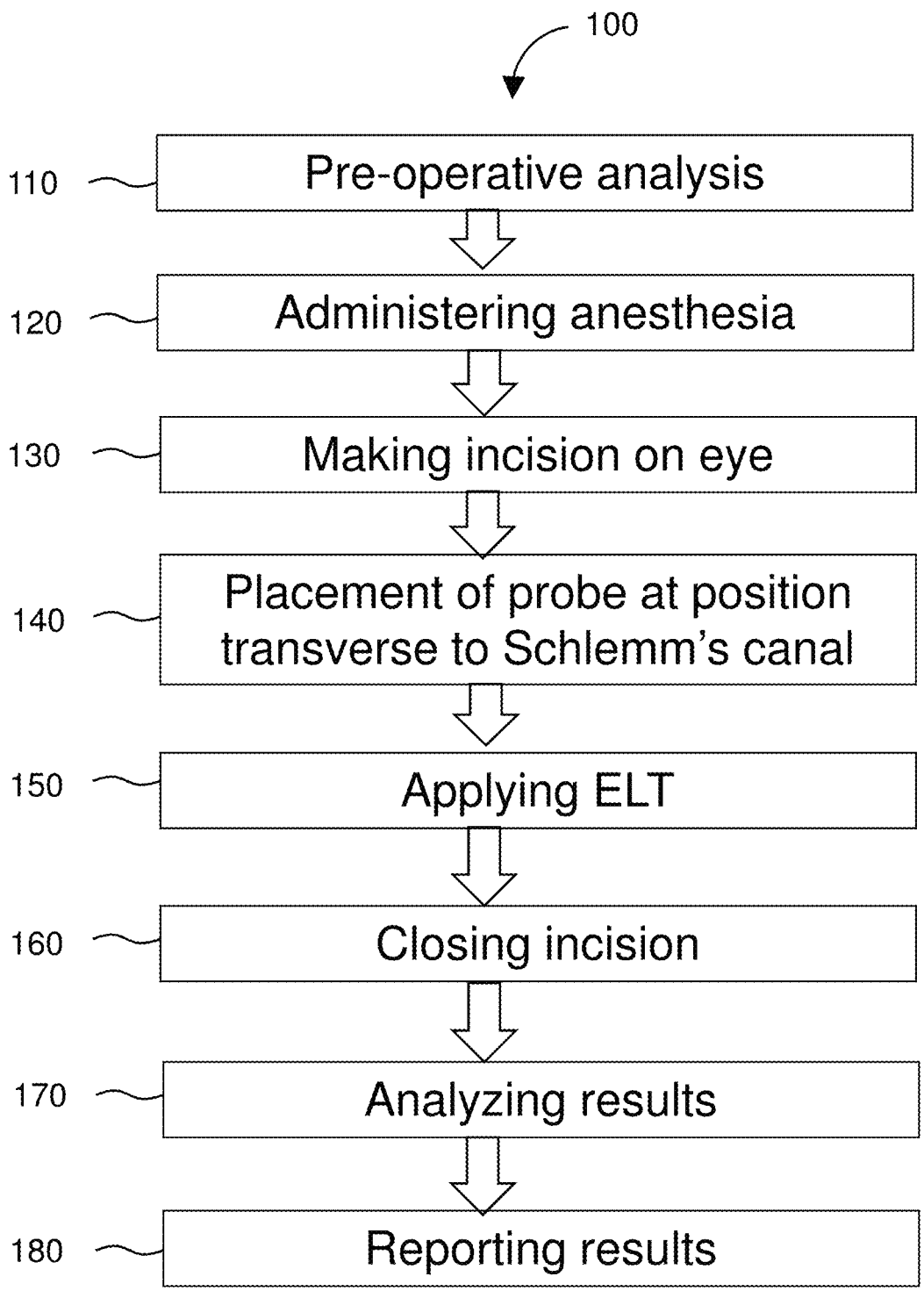
FIG. 1 is a flowchart of an embodiment of methods of the invention.

FIG. 1 shows a flowchart of an embodiment 100 of methods of the invention. Methods of the invention are directed to treating a patient having glaucoma with ELT. In the invention, energy shots from the excimer laser are delivered by a fiber probe at a position transverse to the Schlemm's canal. In some examples, methods include 110 pre-operative analysis, such as diagnosis of the eye condition and inspection and/or visualization of the anterior chamber of the eye to aid in placement of the laser probe. In the invention, excimer laser trabeculostomy (ELT) is used to treat glaucoma.

In some embodiments, the method includes 120 administering anesthesia to the patient. Topical anesthesia is commonly employed, typically by the instillation of a local anesthetic such as tetracaine or lidocaine. Lidocaine and/or a longer-acting bupivacaine anesthetic may be injected into the area surrounding (peribulbar block) or behind (retrobulbar block) the eye muscle cone to more fully immobilize the extraocular muscles and minimize pain sensation. Optionally, a facial nerve block may be performed using lidocaine and bupivacaine to reduce lid squeezing. In some cases, such as for children, patients with traumatic eye injuries, and nervous or uncooperative patients and animals, general anesthesia is administered with cardiovascular monitoring. To prepare the area for surgery, proper sterile precautions must be taken, including use of antiseptics like povidone-iodine and employment of sterile drapes, gowns, and gloves. are employed. In some cases, an eye speculum is inserted to keep the eyelids open.

A physician 130 makes a small incision on the eye of the patient. Before the ELT procedure is performed, a small incision is made in the cornea of the eye to allow introduction of the fiber probe. Typically, the incision is about ⅛ inch or smaller.

During the excimer laser trabeculostomy procedure, a physician guides the delivery tip of the fiber probe through the corneal incision in the eye and towards the trabecular meshwork. The delivery tip is 140 guided by the physician to a position transverse to the Schlemm's canal. A Gonio lens, endoscope, and/or illumination source may be used by the physician to aid in positioning the delivery tip. By providing a laser probe at a position transverse to the Schlemm's canal, or crosswise to the Schlemm's canal, the energy from the excimer laser is delivered to a greater amount of surface area than if the laser was in a parallel or perpendicular position to the Schlemm's canal. Thus, arrangement of the delivery tip at a position transverse to the Schlemm's canal achieves optimal photoablation and formation of perforations in the meshwork and/or Schlemm's canal. The orientation and positioning of the delivery tip is critical when creating perforations in the tissue, as achieving transverse placement of perforations in the meshwork relative to Schlemm's canal provides optimal drainage.

Once the delivery tip is at a position transverse to the Schlemm's canal, the physician 150 applies ELT treatment to the patient by delivering a series of shots of laser energy to the trabecular meshwork and Schlemm's canal. The physician applies pulsed photoablative energy. In some examples, a physician creates about 10 ELT sites in an eye of the patient. In some examples, the physician creates greater than about 10 ELT sites per eye of the patient. A small amount of bloody reflux from Schlemm's canal confirms each opening. The fiber probe is removed from the eye. The IOP decreases immediately after administering the ELT procedure.

After applying ELT treatment, a physician 160 closes the incision. Typically, a physician uses sutures to close the incision. Some physicians place a suture in the incision and other physicians reserve a suture for instances involving persistent leakage.

Methods of the invention include 170 analyzing postoperative results and 180 reporting results and/or scheduling a post-operative follow-up appointment with the patient after surgery. For example, the physician's analysis may include observing a small amount of bloody reflux from Schlemm's canal to confirm each opening. By observing the bloody reflux and drainage of aqueous humor, the physician is able to immediately verify the effectiveness of the laser treatment. In turn, the physician may report the results to the patient, prescribe post-operative medication, such as topical antibiotics and steroid drops, and schedule any follow-up post-operative visits with the patient. Topical antibiotics and steroid drops are typically prescribed and used by the patient for 1 to 2 weeks post-operatively.

Figure 2:
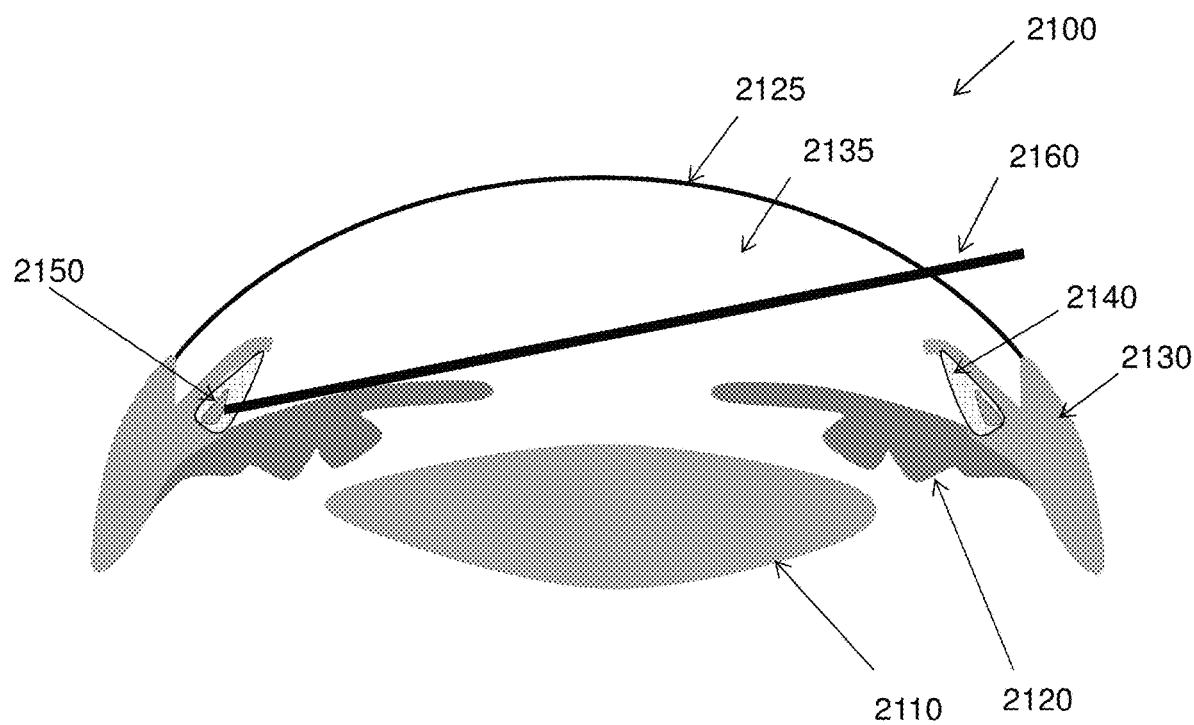
FIG. 2 is a schematic sectional view of an embodiment of the invention in an eye.
Figure 3:
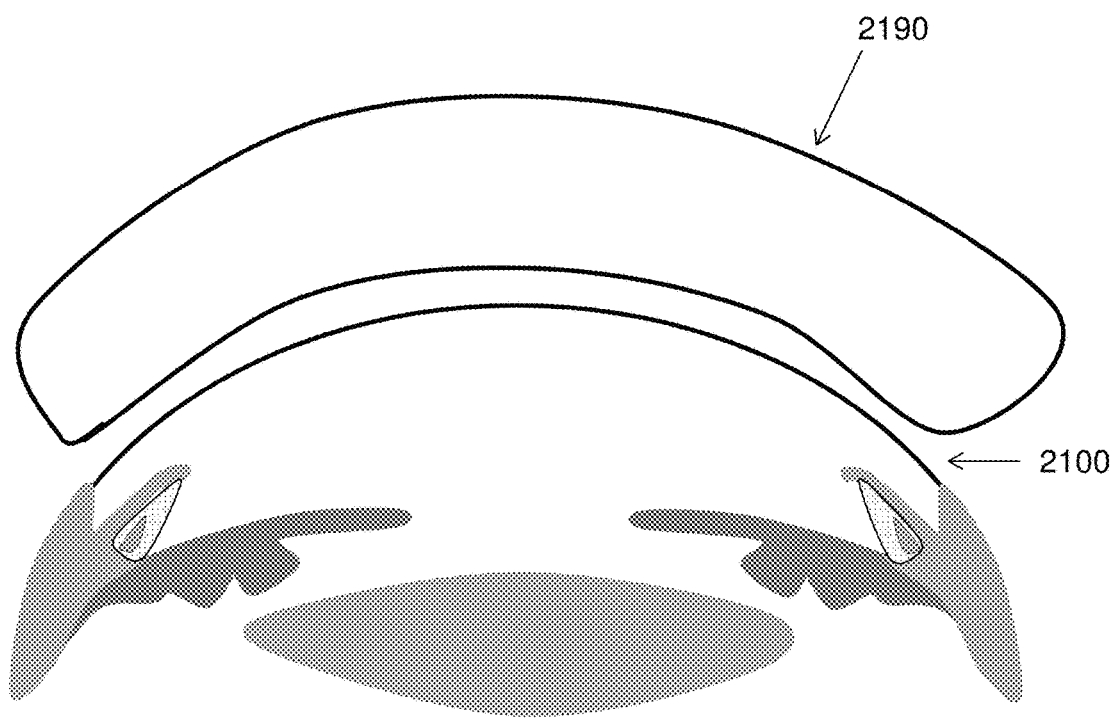
FIG. 3 shows the schematic section view of an eye with a light source aid.
Figure 4:
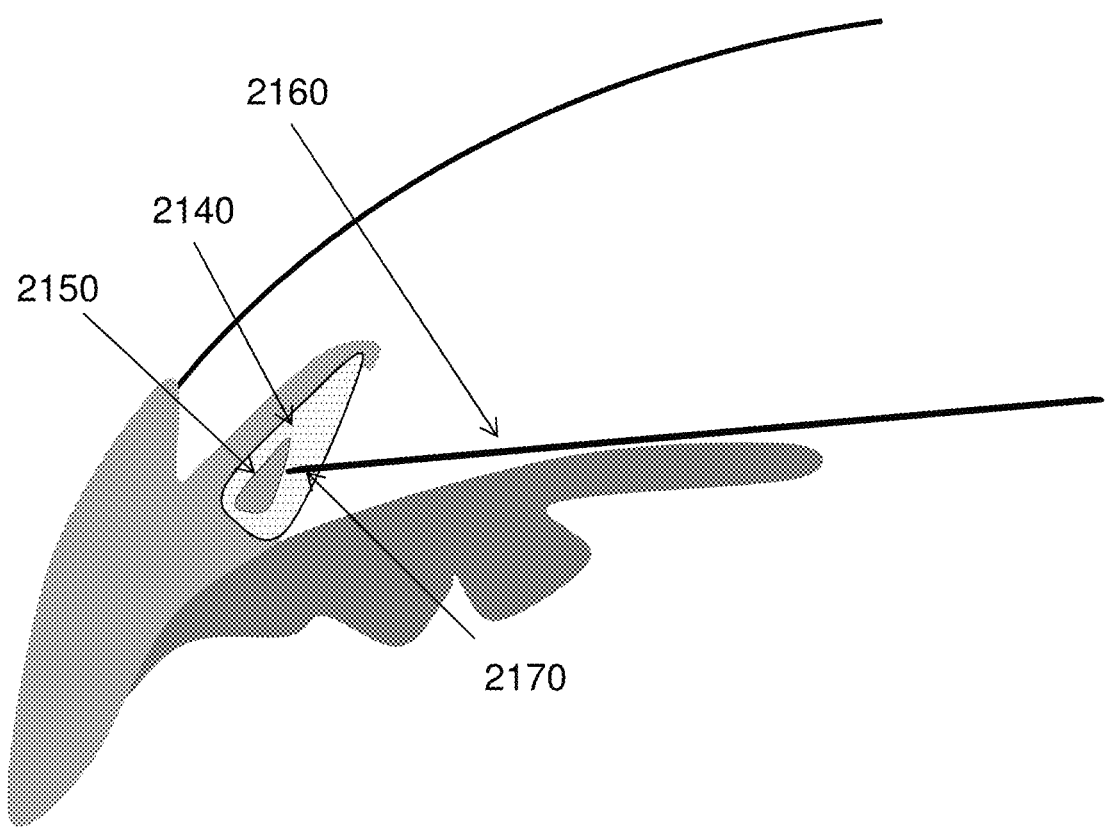
FIG. 4 is an enlarged schematic sectional view of an embodiment of the invention.

FIG. 2 is schematic sectional view of an eye 2100 illustrating the interior anatomical structure. FIG. 3 shows the schematic section view of an eye 2100 with a light source 2190, such as a Gonio lens, endoscope, or other light source. FIG. 4 is an enlarged schematic sectional view of the eye. The outer layer, or sclera, 2130 serves as a supporting framework for the eye, and the front of the outer layer 2130 includes a cornea 2125, a transparent tissue that enables light to enter the eye. An anterior chamber 2135 is located between the cornea 2125 and a crystalline lens 2110, and a posterior chamber is located behind the lens 2110. The anterior chamber 2135 contains a constantly flowing clear fluid called aqueous humor. In the anterior chamber 2135, an iris 2120 encircles the outer perimeter of the lens 2110 and includes a pupil at its center, which controls the amount of light passing through the lens 2110.

The eye further includes a trabecular meshwork 2140, which is a narrow band of spongy tissue that encircles the iris 2120 within the eye. The trabecular meshwork has a variable shape and is microscopic in size. It is of a triangular cross-section and of varying thickness in the range of about 100 microns to about 200 microns. It is made up of different fibrous layers having micron-sized pores forming fluid pathways for the egress of aqueous humor. The trabecular meshwork 2140 has been measured to a thickness of about 100 microns at its anterior edge, known as Schwalbe's line, which is at the approximate juncture of the cornea and sclera.

The trabecular meshwork widens to about 200 microns at its base where it and iris 2120 attach to the scleral spur. The passageways through the pores in trabecular meshwork 2140 lead through very thin, porous tissue called the juxtacanalicular trabecular meshwork that abuts the interior side of a structure called Schlemm's canal 2150. Schlemm's canal 2150 is filled with a mixture of aqueous humor and blood components and branches off into collector channels which drain the aqueous humor into the venous system. Because aqueous humor is constantly produced by the eye, any obstruction in the trabecular meshwork, the juxtacanalicular trabecular meshwork, or in Schlemm's canal prevents the aqueous humor from readily escaping from the anterior eye chamber, resulting in an elevation of intraocular pressure within the eye.

The eye has a drainage system for the draining aqueous humor. The aqueous humor flows from a posterior chamber behind the lens 2110 through the pupil into the anterior chamber 2135 to the trabecular meshwork 2140 and into Schlemm's canal 2150 to collector channels and then to aqueous veins. The obstruction of the aqueous humor outflow which occurs in most open angle glaucoma (i.e., glaucoma characterized by gonioscopically readily visible trabecular meshwork) typically is localized to the region of the juxtacanalicular trabecular meshwork located between the trabecular meshwork 2140 and Schlemm's canal 2150, more specifically, the inner wall of Schlemm's canal. When an obstruction develops, such as at the juxtacanalicular trabecular meshwork or at Schlemm's canal, intraocular pressure gradually increases over time, leading to damage and atrophy of the optic nerve, subsequent visual field disturbances, and eventual blindness if left untreated.

An excimer laser trabeculostomy (ELT) procedure according to the invention is used to treat glaucoma. A delivery tip of a fiber probe 2160 is guided through a small incision, typically about ⅛ inch or smaller, in the cornea 2125 of the eye and across the anterior chamber 2135 to a position transverse to the Schlemm's canal 2150. The fiber probe is coupled to an excimer laser source and transmits laser energy from the laser source to the trabecular meshwork 2140 and Schlemm's canal 2150, resulting in photoablation of tissue including at least the trabecular meshwork 2140 and, in some instances, the Schlemm's canal 2150. The photoablation from the laser energy creates perforations in the meshwork and/or Schlemm's canal, thereby improving fluid drainage into the Schlemm's canal 2150 and reducing intraocular pressure in the eye.

FIG. 4 shows the arrangement of the delivery tip 2160 at a position transverse 2170 to the Schlemm's canal 2150. Arrangement of the fiber probe at a transverse position to the Schlemm's canal allows the laser path to travel crosswise through the trabecular meshwork to the Schlemm's canal. By positioning the fiber probe transverse to the Schlemm's canal, the laser is able to provide photoablation to a greater amount of surface area of the trabecular meshwork in comparison to a fiber probe arranged at positions perpendicular or parallel to the Schlemm's canal. Moreover, if the delivery tip of the fiber probe was positioned parallel to the Schlemm's canal, the laser would not provide photoablation to any surface area of the trabecular meshwork or Schlemm's canal.

Figure 5:
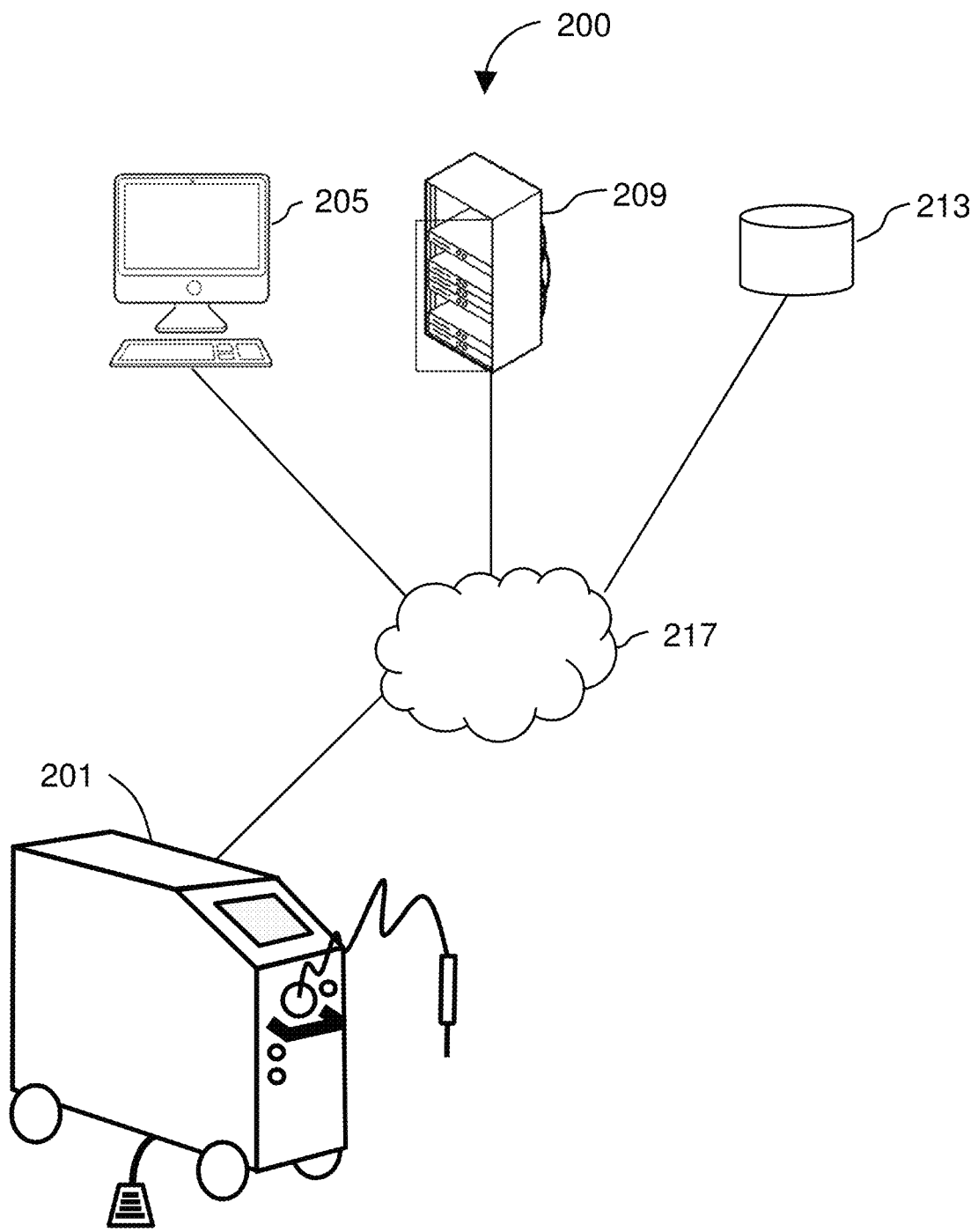
FIG. 5 shows an embodiment of systems of the invention.

FIG. 5 diagrams a schematic of system 200 according to certain embodiments of the invention. The system 200 includes an ELT instrument 201 communicatively coupled to a computer 205. The system 200 optionally includes a server 209 and storage 213. Any of the ELT instrument 201, the computer 205, the server 209, and the storage 213 that are included preferably exchange data via communication network 217. Where methods of the invention employ a client/server architecture, steps of methods of the invention may be performed using the server, which includes one or more of processors and memory, capable of obtaining data, instructions, etc., or providing results via an interface module or providing results as a file. The server may be provided by a single or multiple computer devices, such as the rack-mounted computers sold under the trademark BLADE by Hitachi. In system 200, each computer preferably includes at least one processor coupled to a memory and at least one input/output (I/O) mechanism.

A processor generally includes a chip, such as a single core or multi-core chip, to provide a central processing unit (CPU). A processor may be provided by a chip from Intel or AMD. Memory can include one or more machine-readable devices on which is stored one or more sets of instructions (e.g., software) which, when executed by the processor(s) of any one of the disclosed computers can accomplish some or all of the methodologies or functions described herein. A computer of the invention will generally include one or more I/O device such as, for example, one or more of a video display unit (e.g., a liquid crystal display (LCD) or a cathode ray tube (CRT)), an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem. The system 200 may be used to perform methods described herein. Instructions for any method step may be stored in memory and a processor may execute those instructions.

Figure 6:
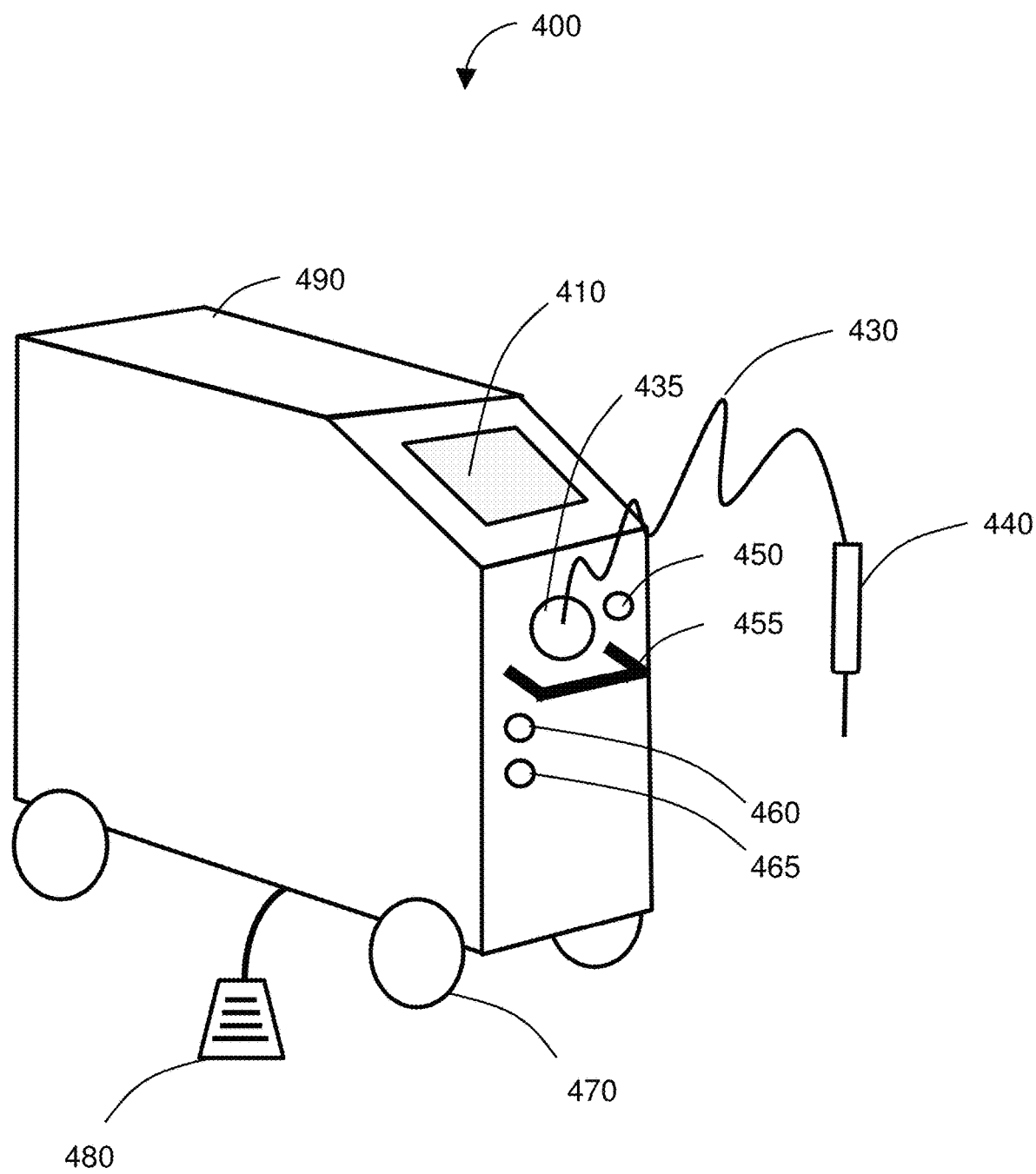
FIG. 6 shows an embodiment of an ELT system.

FIG. 6 shows an embodiment of the excimer laser trabeculostomy (ELT) instrument 400. An excimer laser is contained in the housing 490. The housing has wheels 470 and is portable. The push-pull handle 455 assists with portability of the ELT instrument 400. A foot pedal 480 extends from the housing 490 and is operable to provide power for delivering shots from the laser through the fiber probe 440. The connector 430 of the fiber probe 440 connects to the excimer laser in the housing 490 at the fiber connection port 435. The housing comprises an interactive user interface 410. In some examples, the interactive user interface 410 displays patient information, machine settings, and procedure information. The housing 490 includes control buttons, switches, and dials, such as a holder for a fiber probe cap 450, an emergency stop button 460, and a power switch 465.

Figure 7:
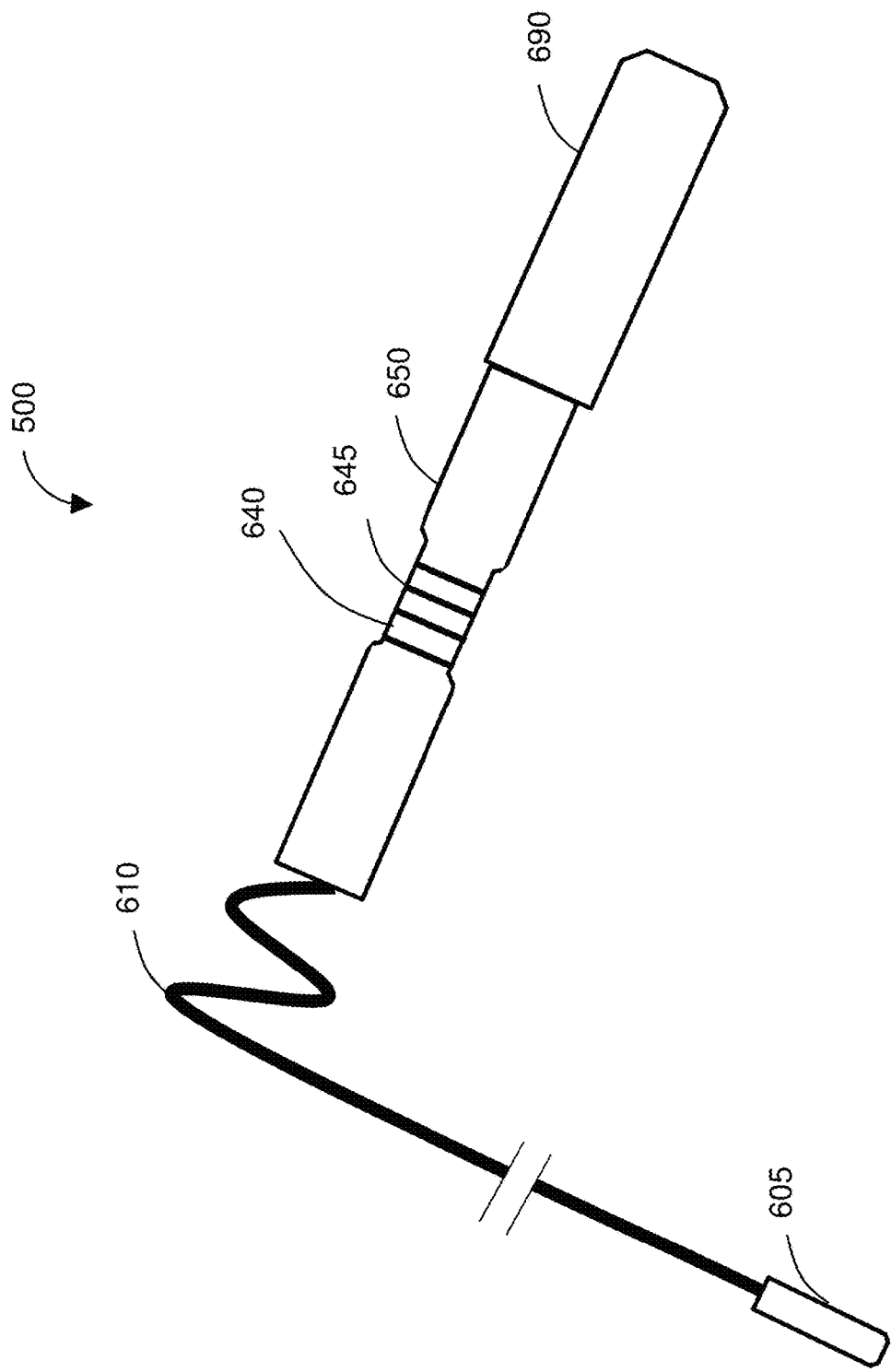
FIG. 7 shows a capped embodiment of a fiber probe.
Figure 8:
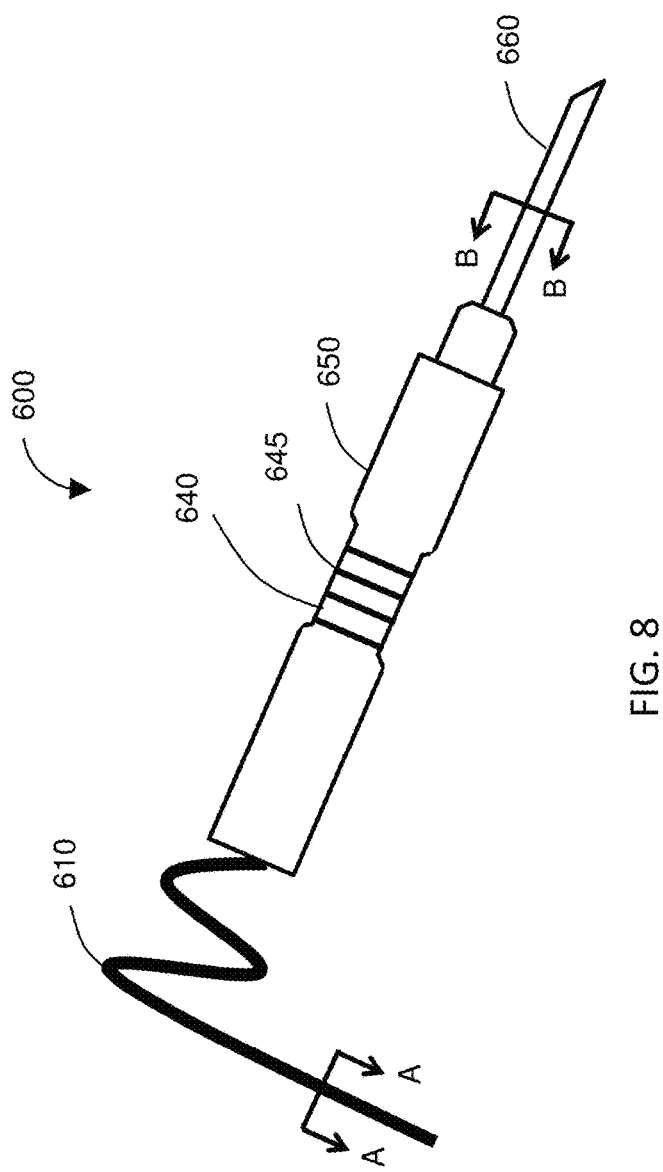
FIG. 8 shows an embodiment of a fiber probe.

FIG. 7 shows a capped version of the fiber probe 500. FIG. 8 shows an uncapped version of the ELT probe or fiber probe 600. The fiber probe 500, 600 comprises an optical fiber 630 that runs through the fiber probe 600 and connects the fiber probe 600 to the excimer laser. The connector 610 comprises the optical fiber 630 surrounded by a protective sheath 620. In an example of the invention, the connector 610 is about 200 cm to about 300 cm in length. A proximal end of the connector has a connection plug 605 that is operable to interact with the connection point on the instrument. In an example, the connection plug 605 has threads that match up with threads on the connection port to secure the connector 610 to the instrument. In an example, the connection plug 605 has a ridge around the plug that matches up with a slot in the connection port to secure the connector 610 to the instrument. The connector 610 connects a connection point on the instrument (such as connection port 435 shown in FIG. 6) to the body 650 of the handheld fiber probe 600.

The fiber probe 600 is sterilized by any suitable method that provides sterilized equipment suitable for use on humans. In some embodiments, the fiber probe 600 is disposable. In some embodiments, the fiber probe 600 has a tag that determines operability. In some examples, a radio frequency identification (RFID) tag must match an RFID on the instrument in order to operate. In an embodiment, the body 650 of the handheld probe is plastic. In an embodiment, the body 650 of the fiber probe 500, 600 is about 5 cm to about 10 cm in length. Preferably, the body 650 of the fiber probe is about 7 cm in length. Optionally, the body may have a finger grip 640 with ridges 645. The fiber tip or delivery tip 660 at the distal end of the fiber probe comprises an optical fiber 630 jacketed in metal 670, such as stainless steel or titanium. The delivery tip, or jacketed fiber at the distal end of the probe, is inserted into the eye and guided to the trabecular meshwork. A foot pedal is depressed to power the excimer laser. When powered, a shot of energy is delivered from the excimer laser that travels through the optical fiber to the trabecular meshwork and Schlemm's canal to create a plurality of perforations in the trabecular meshwork and/or Schlemm's canal.

Figure 10:
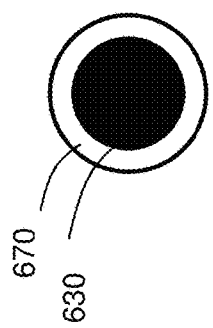
FIG. 10 shows a cross-sectional view of a fiber probe along line B-B of FIG. 8.
Figure 9:
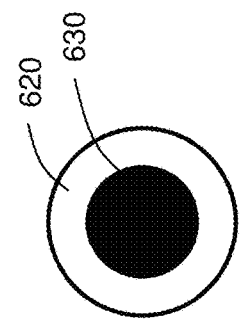
FIG. 9 shows a cross-sectional view of a fiber probe along line A-A of FIG. 8.

FIG. 9 shows a cross-sectional view of the fiber probe across line A-A of FIG. 8. The cross-section shown in A-A is the cross-section of the connector 610 from FIG. 8. A protective sheath 620 surrounds the optical fiber 630. In some examples, the protective sheath is a protective plastic or rubber sheath. FIG. 10 shows a cross-sectional view of the fiber probe across line B-B of FIG. 8. The cross-section shown in B-B is the cross-section of the delivery tip 660 from FIG. 8. A metal jacket 670 covers the optical fiber 630. In some cases, stainless steel is used to jacket the optical fiber in the delivery tip.

INCORPORATION BY REFERENCE

References and citations to other documents, such as patents, patent applications, patent publications, journals, books, papers, and web contents made throughout this disclosure are hereby incorporated herein by reference in their entirety for all purposes.

EQUIVALENTS

While the present invention has been described in conjunction with certain embodiments, one of ordinary skill, after reading the foregoing specification, will be able to effect various changes, substitutions of equivalents, and other alterations to the compositions and methods set forth herein.

What is claimed is:

1. A method of delivering laser energy to a surface of a trabecular meshwork of an eye to treat glaucoma comprising:
    inserting a probe into an eye of a subject having glaucoma;
    adjusting placement of the probe to a position transverse to Schlemm's canal in the eye; and
    creating a plurality of perforations having transverse placement in the trabecular meshwork relative to the Schlemm's canal of the eye by applying a plurality of shots from an excimer laser source, wherein the plurality of perforations are created in the trabecular meshwork in order to treat the glaucoma.

2. The method of claim 1, wherein a light source aids in adjusting placement of the probe.

3. The method of claim 2, wherein the light source is a Gonio lens, endoscope, or other illumination source.

4. The method of claim 1, wherein the plurality of shots comprises 10 shots per eye.

5. The method of claim 1, wherein the plurality of shots comprises greater than 10 shots per eye.

6. The method of claim 1, wherein each perforation has a diameter of 200 µm.

7. The method of claim 1, wherein the probe is inserted into an incision in the eye.

8. The method of claim 7, wherein the incision has a length of about ⅛ inch or smaller.

9. The method of claim 1, further comprising administering anesthesia to the subject before inserting the probe.

10. The method of claim 1, further comprising analyzing effectiveness of the shot by visualizing drainage of aqueous humor and bloody reflux.

11. The method of claim 1, wherein the probe is a fiber probe.

12. The method of claim 11, wherein a delivery tip of the fiber probe comprises an optical fiber jacketed in a metal.

13. The method of claim 12, wherein the metal is stainless steel.

14. The method of claim 12, wherein the delivery tip is beveled.

15. The method of claim 1, wherein the excimer laser source comprises a xenon chloride laser.

16. The method of claim 1, further comprising physically contacting the trabecular meshwork with the probe, wherein the plurality of perforations are created while the probe is physically contacting the trabecular meshwork.

17. The method of claim 1, wherein at least one of the plurality of perforations creates a fluid path from a front chamber of the eye through the trabecular meshwork to the Schlemm's canal.

18. The method of claim 1, further comprising removing the probe after the creating of the plurality of perforations.

19. A method of delivering laser energy to a surface of a trabecular meshwork of an eye to treat glaucoma comprising:
- inserting a probe into an eye of a subject having glaucoma;
- adjusting placement of the probe to a position transverse to Schlemm's canal in the eye;
- physically contacting the trabecular meshwork with the probe; and
- creating a plurality of perforations having transverse placement in the trabecular meshwork relative to the Schlemm's canal of the eye by applying a plurality of shots from an excimer laser source, wherein the plurality of perforations are created in the trabecular meshwork in order to treat the glaucoma.

* * * * *